United States Patent
Jadidian et al.

(10) Patent No.: US 12,073,021 B1
(45) Date of Patent: Aug. 27, 2024

(54) CONDUCTIVE MATTER MOVEMENT TRACKING USING RF SENSORS

(71) Applicant: Microsoft Technology Licensing, LLC, Redmond, WA (US)

(72) Inventors: Jouya Jadidian, Los Gatos, CA (US); Gabriele D'Amone, Mountain View, CA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 18/170,313

(22) Filed: Feb. 16, 2023

(51) Int. Cl.
| | |
|---|---|
| *G06F 3/01* | (2006.01) |
| *A61B 5/00* | (2006.01) |
| *A61B 5/05* | (2021.01) |
| *A61B 5/11* | (2006.01) |
| *G06T 11/00* | (2006.01) |

(52) U.S. Cl.
CPC ............... *G06F 3/014* (2013.01); *A61B 5/05* (2013.01); *A61B 5/1126* (2013.01); *A61B 5/6826* (2013.01); *G06T 11/00* (2013.01)

(58) Field of Classification Search
CPC ......... G06F 3/014; A61B 5/05; A61B 5/1126; A61B 5/6826; G06T 11/00
See application file for complete search history.

(56) References Cited

U.S. PATENT DOCUMENTS

| | | | | |
|---|---|---|---|---|
| 2016/0349790 | A1* | 12/2016 | Connor | G06F 3/017 |
| 2021/0382554 | A1* | 12/2021 | Colachis | A61N 1/36031 |
| 2021/0401307 | A1 | 12/2021 | Turner | |

FOREIGN PATENT DOCUMENTS

| | | |
|---|---|---|
| CN | 113869180 A | 12/2021 |
| GB | 2584420 A | 12/2020 |

OTHER PUBLICATIONS

Invitation to Pay Additional Fees received for PCT Application No. PCT/US2024/014912, May 22, 2024, 13 pages.
Kim, et al., "Etherpose: Continuous Hand Pose Tracking with Wrist-Worn Antenna Impedance Characteristic Sensing", Proceedings of the 35th Annual ACM Symposium on User Interface Software and Technology, Oct. 29-Nov. 2, 2022, 12 pages.
International Search Report and Written Opinion received for PCT Application No. PCT/US2024/014912, Jul. 15, 2024, 23 pages.

* cited by examiner

*Primary Examiner* — Peter D McLoone
(74) *Attorney, Agent, or Firm* — Workman Nydegger

(57) ABSTRACT

A wearable device that tracks body movement is disclosed. The device includes a housing and a connection member. The connection member is coupled to the housing, and the connection member enables the device to be coupled to a user's body part. This body part is associated with the conductive matter. The device includes an RF sensor in the housing. The RF sensor oscillates at a preselected frequency. The RF sensor is tuned to resonate when the RF sensor is located a preselected distance from the conductive matter. As the conductive matter moves closer or farther from the RF sensor based on user movement, a resulting waveform generated based on data from the RF sensor is modified, and the resulting waveform is usable to determine how the user moved.

20 Claims, 17 Drawing Sheets

CONDUCTIVE MATTER MOVEMENT TRACKING USING RF SENSORS

BACKGROUND

Mixed-reality (MR) systems, which include virtual-reality (VR) and augmented-reality (AR) systems, have received significant attention because of their ability to create truly unique experiences for their users. For reference, conventional VR systems create completely immersive experiences by restricting their users' views to only virtual environments. This is often achieved through the use of a head mounted device (HMD) that completely blocks any view of the real world. As a result, a user is entirely immersed within the virtual environment. In contrast, conventional AR systems create an augmented-reality experience by visually presenting virtual objects that are placed in or that interact with the real world.

As used herein, VR and AR systems are described and referenced interchangeably. Unless stated otherwise, the descriptions herein apply equally to all types of MR systems, which (as detailed above) include AR systems, VR reality systems, and/or any other similar system capable of displaying virtual content.

An MR system can be used to display various different types of information to a user. Some of that information is displayed in the form of augmented reality or virtual reality content, which can also be referred to as a "hologram." That is, as used herein, the term "hologram" generally refers to image content that is displayed by the MR system. In some instances, the hologram can have the appearance of being a three-dimensional (3D) object while in other instances the hologram can have the appearance of being a two-dimensional (2D) object.

MR headsets/HMDs have now become a consumer technology, with the hope that their uniquely immersive display and interaction systems will lead to more compelling entertainment, productivity, and telepresence applications. Users are often provided the opportunity to interact with holograms displayed by the MR system. There are various existing technologies for detecting how hands move, such as how they move in order to interact with a hologram. Existing sensing technologies are largely focused on either image analysis or detecting skin displacement, movement, or directionality via reliance on strain gauge sensors.

Such technologies are deficient, however, in that they cannot fully monitor the user's movements. For instance, if the user's hand moves outside of the field of view (FOV) of a hand tracking camera, then the MR system will not be able to use image analysis to track the user's hand movement. With regard to strain gauge sensors, such sensors require close contact with the user's skin and need to extend along the whole surface being sensed, thereby making them cumbersome and not ideal for many wearable applications. What is needed, therefore, is an improved technique for tracking how a user moves.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Embodiments disclosed herein relate to systems, devices, and methods relating to the use of a wearable device comprising radio frequency (RF) sensors that track movement of conductive matter in or on a user's body.

Some embodiments are directed to a wearable device that monitors movement of conductive matter (e.g., a muscle group, blood, salt water, or perhaps even a topical conductive cream) of a user who is wearing the device. The device includes a housing and a clip or connection member. The clip or connection member is attached to the housing, and the clip or connection member enables the wearable device to be coupled to a body part of the user. This body part is associated with the conductive matter. The device also includes a radio frequency (RF) sensor that is disposed in the housing. The RF sensor is caused to oscillate at a preselected frequency. The RF sensor is tuned to resonate when the RF sensor is located a preselected distance from the user's conductive matter while the wearable device is clipped to the user's body part. As the conductive matter moves closer or farther from the RF sensor based on the movement of the conductive matter, a resulting waveform generated based on data from the RF sensor is modified, and the resulting waveform is usable to determine how the conductive matter moved.

Some embodiments modify an image file of a body part of a user to reflect a movement of the user's body part. For instance, some embodiments access an image file that represents the user's body part. The image file includes a set of coefficients that, if modified, changes an appearance of the user's body part as represented by the image file. The embodiments obtain scattering parameter data from a radio frequency (RF) sensor disposed on a wearable device worn on the user's body part. The RF sensor generates a set of scattering parameters that reflect a movement of conductive matter associated with the user's body part. The embodiments use a model (e.g., perhaps a deterministic model) and the scattering parameters to update the set of coefficients, resulting in a change to the appearance of the user's body part as represented by the image file.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which.

DETAILED DESCRIPTION

Figure 1:
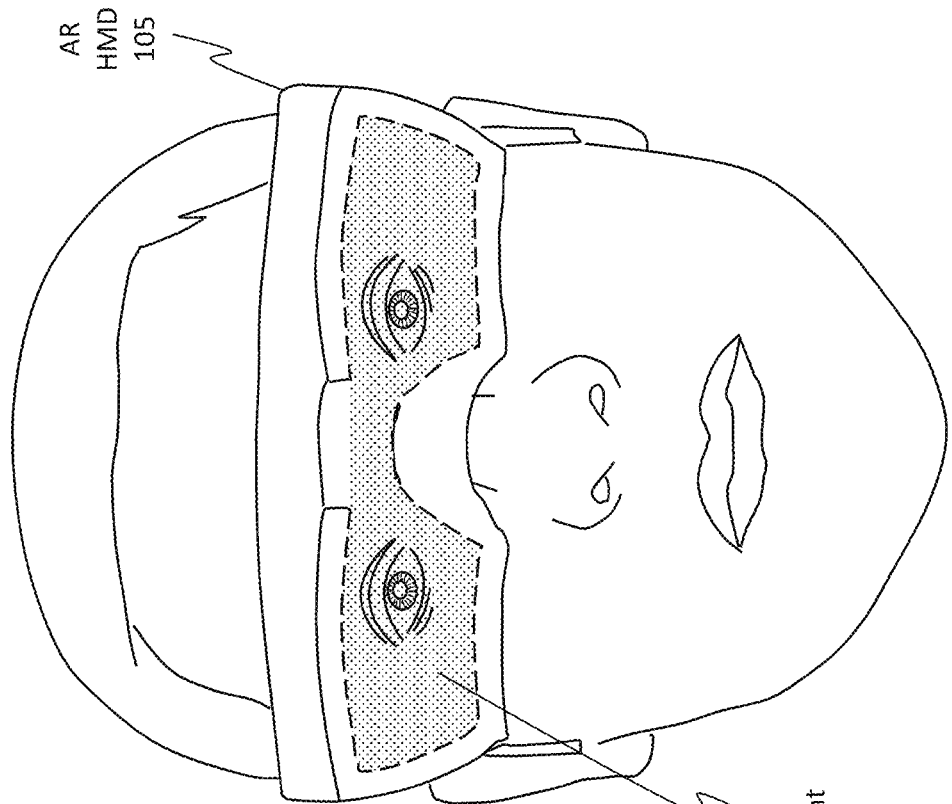
FIG. 1 illustrates various different implementations of a mixed-reality (MR) device, including a VR device and an AR device.
Figure 1:
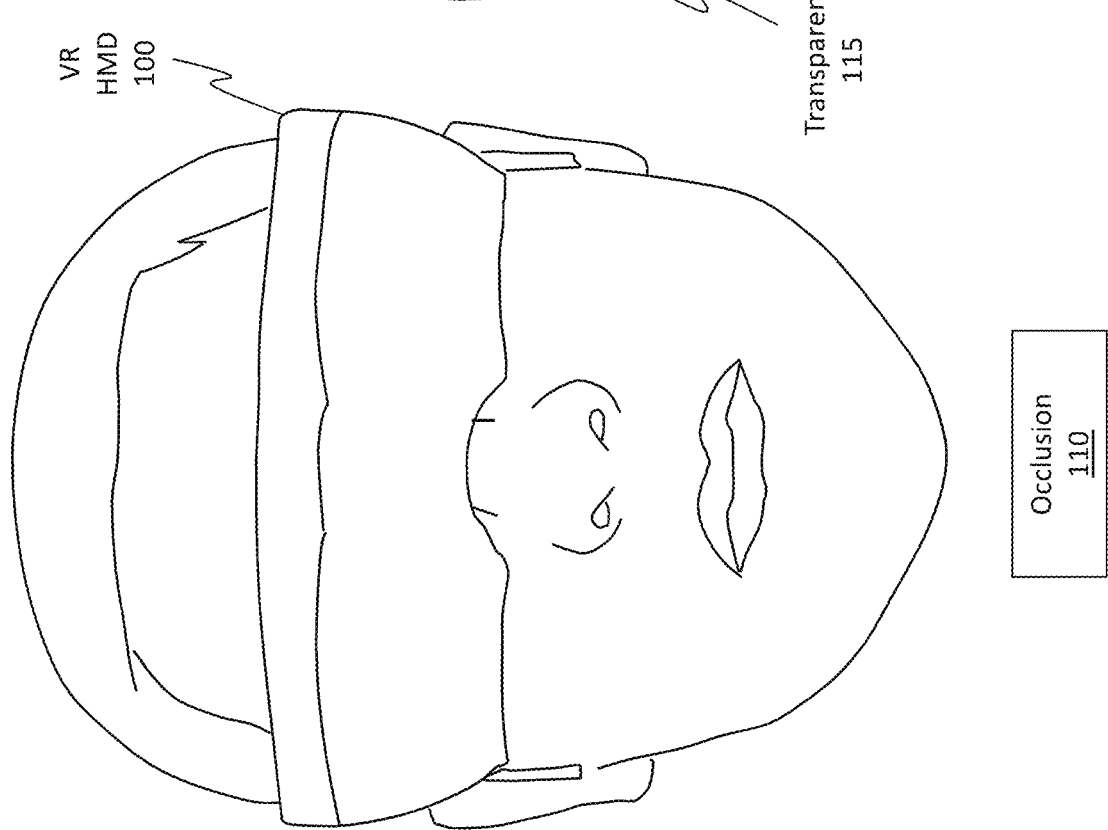

Embodiments disclosed herein relate to systems, devices, and methods relating to the use of a wearable device comprising radio frequency (RF) sensors that track movement of conductive matter in or on a user's body.

Some embodiments are directed to a wearable device that monitors movement of conductive matter (e.g., a muscle group, blood, salt water, or even a conductive topical ointment or cream disposed on top of the user's skin) of a user who is wearing the device. The device includes a housing and a clip or connection member. The clip or connection member is attached to the housing, and the clip or connection member enables the wearable device to be coupled to a body part of the user. This body part is associated with the conductive matter. The device also includes a radio frequency (RF) sensor that is disposed in the housing. The RF sensor is caused to oscillate at a preselected frequency. The RF sensor is tuned to resonate when the RF sensor is located a preselected distance from the user's conductive matter while the wearable device is clipped to the user's body part. As the conductive matter moves closer or farther from the RF sensor based on the movement of the conductive matter, a resulting waveform generated based on data from the RF sensor is modified, and the resulting waveform is usable to determine how the conductive matter moved.

Some embodiments modify an image file of a body part of a user to reflect a movement of the user's body part. For instance, some embodiments access an image file that represents the user's body part. The image file includes a set of coefficients that, if modified, changes an appearance of the user's body part as represented by the image file. The embodiments obtain scattering parameter data from a radio frequency (RF) sensor disposed on a wearable device worn on the user's body part. The RF sensor generates a set of scattering parameters that reflect a movement of conductive matter associated with the user's body part. The embodiments use a model (e.g., perhaps a deterministic model) and the scattering parameters to update the set of coefficients, resulting in a change to the appearance of the user's body part as represented by the image file.

Examples of Technical Benefits, Improvements, and Practical Applications

The following section outlines some example improvements and practical applications provided by the disclosed embodiments. It will be appreciated, however, that these are just examples only and that the embodiments are not limited to only these improvements.

The disclosed embodiments provide numerous benefits, advantages, and practical applications to the technical field of smart, wearable technology. In particular, the disclosed embodiments use radio frequency (RF) tracking technology to monitor a movement of a user's body part or conductive matter, such as the user's muscle group, blood, salt water, or even perhaps a conductive topical cream that is rubbed on the user's skin. This RF technology accurately tracks, in real-time, body movements.

Additionally, the disclosed embodiments are beneficially directed to a type of compact system for detecting body part displacement using a wearable device mounted on the user's body. Movement, displacement, speed, and/or absolute distance of a specific body part can be determined using the disclosed radio frequency (RF) near-field sensing antennas coupled to the enclosure or housing of the wearable device. The data from these sensors can be used to determine an input from the user in the context of a MR scene that is visualized for the user by the MR device.

In some cases, the input will relate to a physical interaction between the body part and an external object. The embodiments are able to estimate the intensity or amount of force that is exerted from the body part onto the object or vice versa.

In this manner, the embodiments are directed to a contact-free sensing approach, which enables the detection of a variety of different body movements without needing a sensor that extends along an entire surface of the user's body part and even without being in full, direct contact with the user's skin.

Example MR Systems and HMDs

Attention will now be directed to FIG. 1, which illustrates an example of a head-mounted mixed-reality (MR) system implemented in two different forms. The head-mounted MR system can also simply be referred to as an MR system, MR device, or a head-mounted device (HMD). In particular, FIG. 1 shows one implementation of the MR system in the form of a virtual-reality (VR) HMD 100. FIG. 1 shows a second implementation of the MR system in the form of an augmented-reality (AR) HMD 105. It should be noted that while a substantial portion of this disclosure is focused on the use of a VR HMD (aka VR device), the embodiments can be implemented using any type of MR device, including VR devices and AR devices.

The VR HMD 100 is shown as being structured so as to either completely or at least mostly occlude the user's view of the real world, as shown by occlusion 110. In contrast, the AR HMD 105 is shown as being structured with a display that enables the user to view the real world. For instance, the display can be transparent 115, thereby enabling the user to see the real world through the display. Generally, the disclosed MR systems are able to display a scene for the user, where that scene can include interactable holograms.

As will be described in more detail later, an MR system can communicate with a different wearable device, which is structured to track various movements of a user's body part, and more particularly, track the movements of conductive matter (e.g., a muscle group, blood, salt water, etc.) in or on the user's body part. The wearable device can be used to enable the user to interact with various different holograms that are displayed by the MR system, as shown in FIG. 2.

Figure 2:
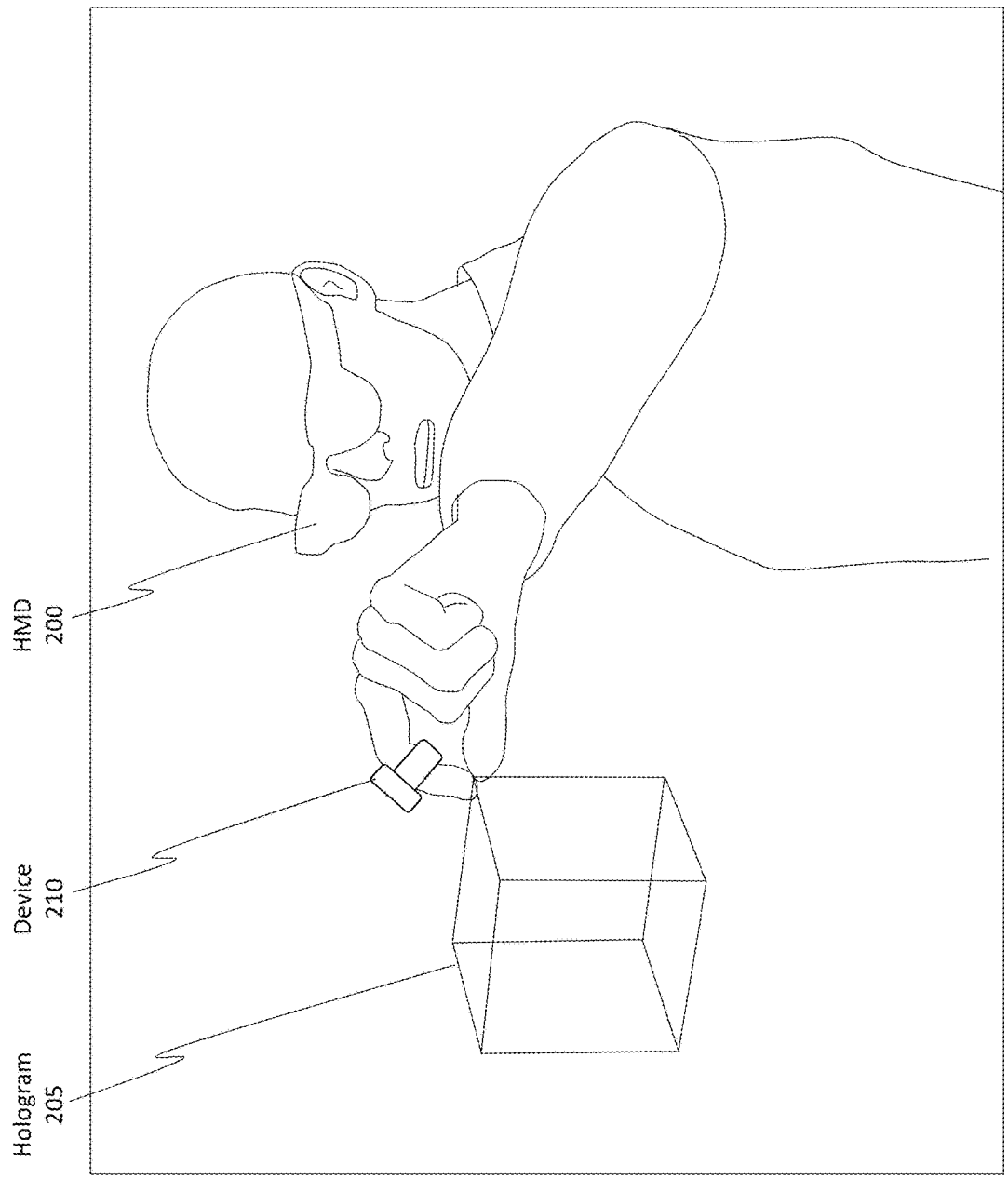
FIG. 2 illustrates an example of how a wearable device can communicate with an MR HMD to enable the user to interact with a hologram.

FIG. 2 shows an example HMD 200, which is representative any one of the VR HMD 100 or AR HMD 105 of FIG. 1. HMD 200 is currently shown as displaying a hologram 205 that can be manipulated by the user wearing the HMD 200. This manipulation can optionally occur via use of a wearable device 210, that is separate and physically distinct from the HMD 200. Notice, the device 210 is currently clipped to the user's finger. One will appreciate, however, how the device 210 can be worn on or clipped to any part of the user's body.

RF Sensors

Figure 3A:
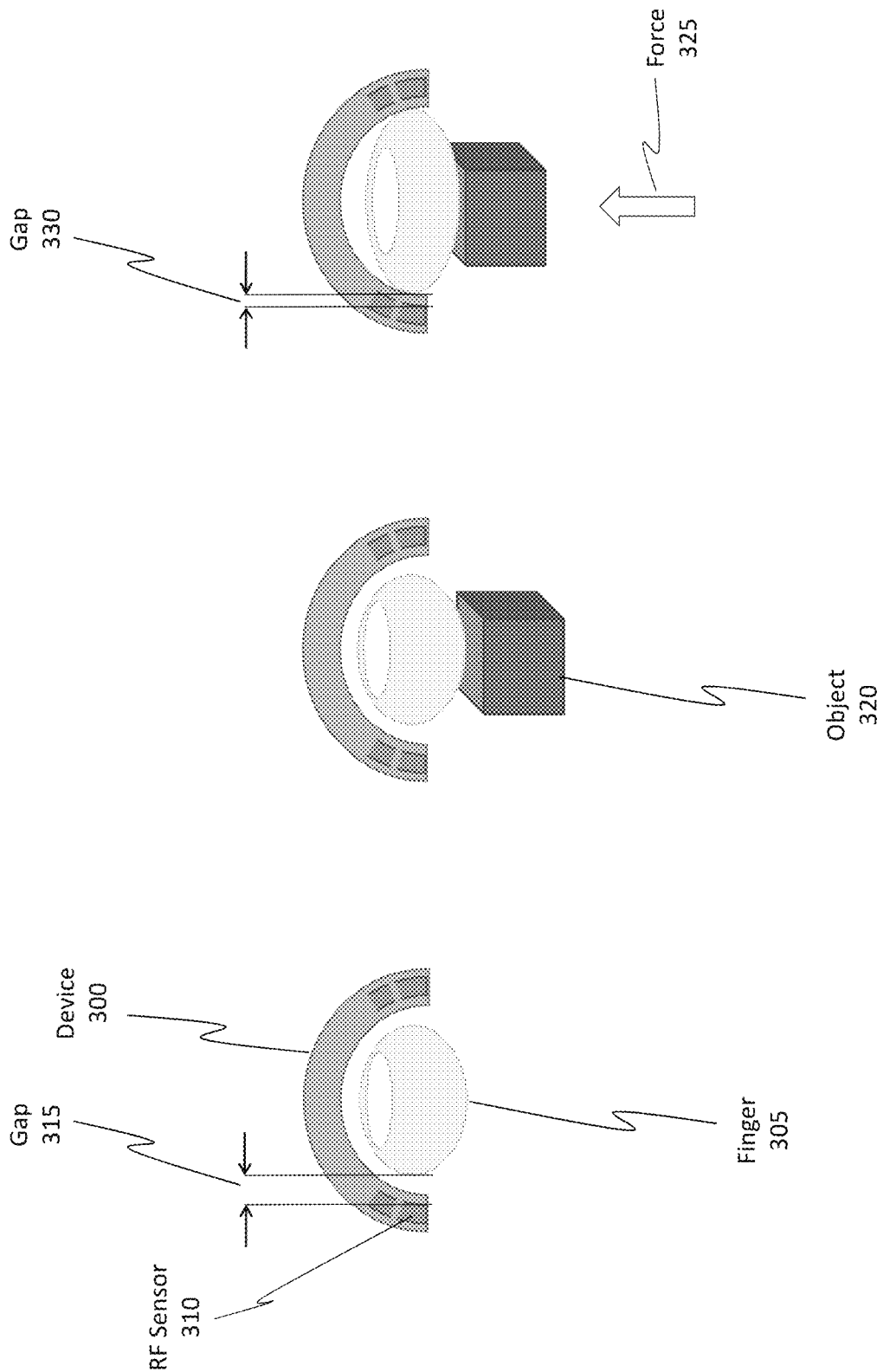
FIGS. 3A, 3B, and 3C illustrate various features of the wearable device.

FIG. 3A shows a device 300, which is representative of the device 210 from FIG. 2. In this scenario, the device 300 is clipped to the user's finger 305. The device 300 includes one or more radio frequency (RF) sensors, such as RF sensor 310.

The RF sensors can be positioned at various locations in the device 300. From these RF sensors, the embodiments are able to understand different movements and displacements of whatever body part the device 300 is attached to. In particular, the RF sensors track movement of conductive matter in the user's body. Examples of such conductive matter include the user's muscle groups, blood, salt water, or even conductive cream that is rubbed onto the user's skin.

Generally, a person's skin itself is not very conductive, so the RF sensor typically does not track movements of the user's actual skin. Instead, the RF sensors are able to track the conductive material that lies underneath the user's skin or perhaps on top of the user's skin. In some embodiments, the wearable device can also be used to track various different health metrics of the user. For instance, the health metrics can include one or more of: blood pressure of the user, heart rate of the user, respiration rate of the user, glucose level of the user, or a hydration level of the user.

The RF sensors operate in the near field region or the midfield region. In effect, the RF sensors operate as a type of resonator. The RF sensors are caused to oscillate at a specific frequency. Notably, the selected frequency can be any frequency. The selected frequency can be selected from a range of available frequencies, as will be described in more detail shortly.

If multiple devices are operating near one another, the RF sensors for each device can be caused to oscillate at a different frequency so as to not interfere with one another. Examples of such frequencies include, but certainly are not limited to one megahertz, one gigahertz, or any other selected frequency. In some cases, the available preselected frequencies are selected from a range of frequencies spanning anywhere between and including about 100 KHz to about 2 GHz. As a more specific example, the selected frequency at which an RF sensor may oscillate can be one of 200 KHz, 500 KHz, 1 GHz, and so on.

The RF sensors also do not necessarily need to contact the user's body, though the device 300 housing the RF sensors will likely be in contact with the user's body. The RF sensors can sit a distance from the user's body part, as shown by the gap 315 in FIG. 3A. For example, the RF sensors can be at a distance of about a few millimeters (e.g., 1-10 mm) away from the user's body to about one inch or 1.5 inches from the user's body. In some cases, the RF sensor may contact the user's body or in very close proximity (e.g., less than 1.0 mm).

In any event, the distance that is created by this gap 315 does not strictly matter because the distance constitutes an impedance between the RF sensors and the user's body part. It can also be assumed that the RF sensors are grounded via the device's contact with the user's body. Further details on grounding will be provided later.

When the user's body part (e.g., finger 305) moves relative to the RF sensors (e.g., either towards them or away from them), a different RF signal will be generated by the RF sensors. For instance, FIG. 3A shows a scenario involving an object 320 coming into contact with the user's finger 305. This object can be a different finger of the user, another body part, or any other object, even one not associated with the user's body. The object 320 exerts a force 325 on the user's finger 305, resulting in a movement to or displacement of the user's finger 305. As a result of this movement, the size of the gap changes, as shown by the difference in size between gap 330 and gap 315. The RF sensor is able to monitor the movement of the user's conductive matter by determining the distance that the conductive matter is relative to the RF sensor 310. Therefore, as the pinching action in FIG. 3A continues or intensifies, the finger's sides get closer and closer to the RF sensors, resulting in the report of different RF signal values.

Figure 3B:
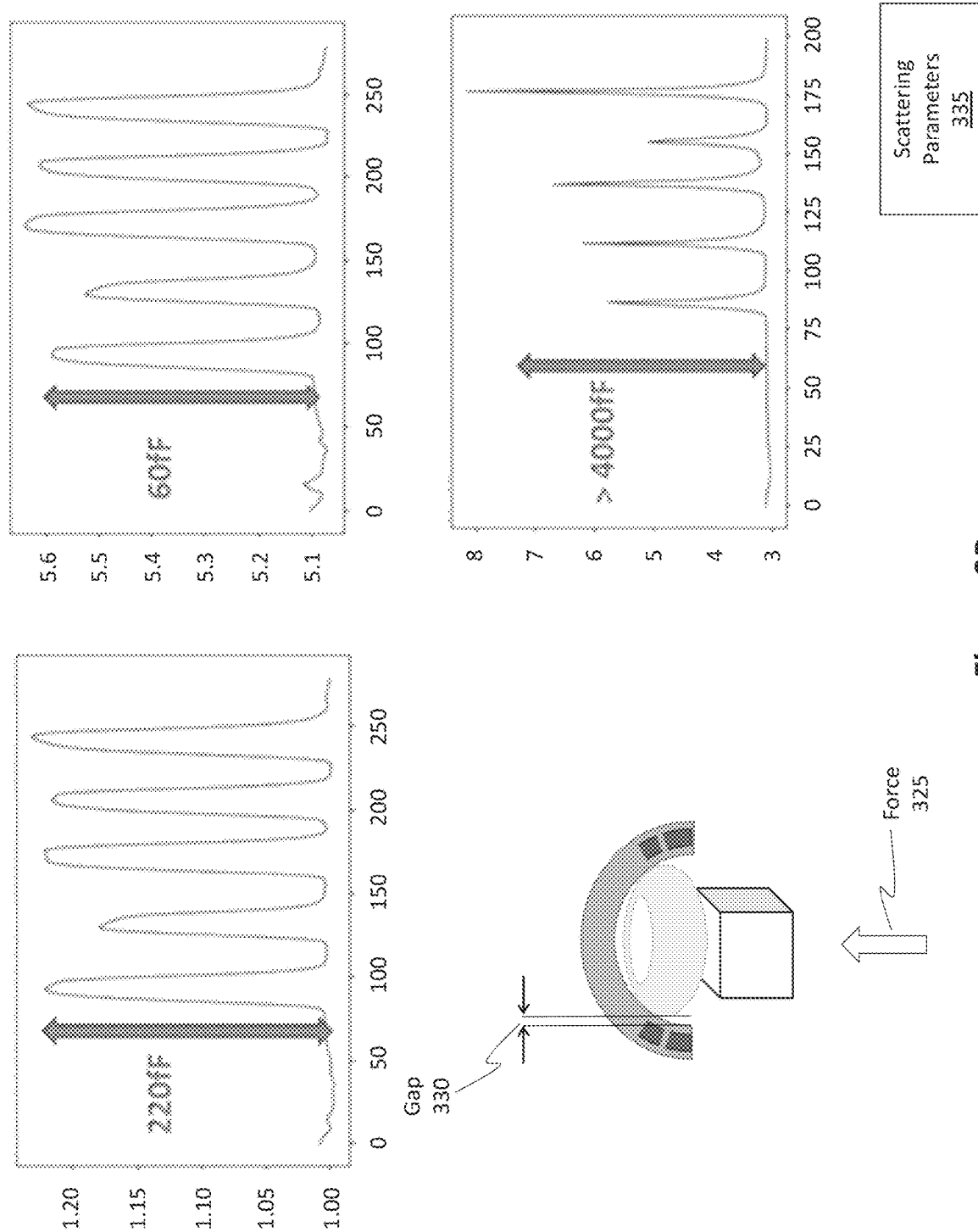

The resulting RF signal generated based on data from the RF sensor 310 will either go up or down depending on the direction of the body part movement. For instance, FIG. 3B shows various different plots that have peaks and valleys. These peaks and valleys correspond to the generated RF signal and represent movements of the user's conductive matter in relation to the RF sensor.

In this manner, the embodiments are directed to various RF sensors that are tuned to be resonating at a selected frequency. When the user's body part is at a so-called "resting pose" ("resting pose" is a pose that can be thought of as a default pose or an initial baseline pose of the user's body part), the RF sensors will not resonate. As soon as the user's body part moves, the signal moves either towards resonance or away from resonance, as shown in FIG. 3B. It should also be noted how the parameters of the circuit (i.e. scattering parameters 335) will change. The embodiments are able to utilize a peak detector to monitor the changes to these scattering parameters 335. The peak detector can detect the peaks and valleys of the plots shown in FIG. 3B and use that data to determine how the user moved.

FIG. 3B shows how the signal changes in response to various different movements. The scattering parameters 335 capture the changes in signal. In FIG. 3B, an RF sensor is disposed near the user's finger. As the finger moves, the RF sensors detect this movement, and the scattering parameters 335 are updated.

In FIG. 3B, the signal is displayed in terms of femto-Farad. This was done simply for convenience purposes, and the RF sensor should not be confused with a traditional sensor used in capacitance touch devices. The disclosed embodiments are able to acquire the signal data and then feed that signal data to a deterministic model, as will be described in more detail later.

By way of further explanation, the embodiments use RF sensors that characterize the scattering parameters of the circuit. The RF sensors can also be thought of as generating an impedance matrix.

With traditional capacitive sensors, these traditional sensors are actually looking at a matrix of capacitances between electrodes, called differential lines. For example, with a smart device having a touch screen, that touch screen includes multiple different lines of conductors that go over the screen, called drive and sense. When a finger comes in between those lines or closely approaches those lines, the capacitance between those lines in either part of the matrix will change and the device has a location of the touch or multi touch input. Notably, this type of touch screen is a completely closed system and does not rely on a ground.

The disclosed RF sensors, on the other hand, are not looking for capacitance; instead, the sensors are looking for a voltage at a certain frequency. The RF sensors are tuned to resonate when the user's body (or rather, the conductive matter in the user's body) is at a very specific distance relative to the RF sensor. Furthermore, the disclosed system is grounded to the user's body because the device housing the RF sensors is a wearable device. In this regard, the user's body acts as a ground, which is in complete contrast with traditional touch screen devices. Traditional touch screen devices attempt to avoid a dependency on the ground because they are often used in multiple different scenarios and conditions (e.g., on top of a table, in a person's pocket, or in a person's hand). The disclosed embodiments, on the other hand, work on the user's body. For instance, the RF sensor can be disposed on a user's ring, wristband, or even an HMD. Accordingly, the wearable device can be grounded to the user.

Another distinction between the disclosed RF sensors and a traditional touch screen device is that touch systems operate at a very specific, standardized frequency. The disclosed RF sensors, on the other hand, are free to operate at any frequency (e.g., 1 GHz, 200 KHz, etc.). The embodiments select a frequency to use. Additionally, the embodiments can perform frequency hopping or spread spectrum, thereby enabling the embodiments to operate in proximity to any number of other devices without causing interference. Stated differently, the RF sensor can be caused to perform frequency hopping. This ability is available because the embodiments are performing peak detection, which is not frequency dependent. Once the signal information is passed from the analog domain to the digital domain, the embodiments can simply look at the amplitude and/or phase.

With regard to the scattering parameter values or impedance, those parameters have four dimensions. One dimension is capacitance or capacity. It is often the case that the dominant factor for this implementation is capacitance, which is why capacitance was used in the illustration of FIG. 3B. Furthermore, operating in capacitive mode acts to lower the power usage because little or no current is flowing when the user's body part is in the resting pose. That is, when the user is in the resting pose, no current is flowing in the circuit so the power consumption is practically zero. In this sense, capacitance in this particular application is the dominant factor of the scattering parameters, but essentially the embodiments are doing scattering parameter peak detection.

By way of more detail regarding the scattering parameters, the scattering parameter matrix is basically defined as the power coming out of a port divided by the power going into another port. If there is a single port, then there will be just a single scattering parameter, which is just S11 (e.g., the reflection coefficient of impedance between the source end and the load end). It is possible to convert S11 to impedance, so impedance has 4 values, one is capacitance, one is inductance, one is conductance, and the final one is resistance. These parameters can be viewed in the following way: series resistance, series inductance, parallel capacitance, and parallel conductance. In the disclosed embodiments, conductance, resistance, and inductance are typically negligible and they can be assumed to be zero just to simplify the calculation pipeline.

Once the capacitance is known, it is possible to just assume that the other three scattering parameters are either zero or infinity. That is, it is possible to assume that conductance and inductance are zero and resistance is infinity. So it turns out that the embodiments are able to just work with a single capacitance for the purpose of synthesizing the signals.

The embodiments thus use the scattering parameters to generate a waveform which is primarily based on the capacitance. That waveform is then fed into a model (e.g., perhaps a deterministic model, as will be described more detail later), which translates or correlates the waveform to actual body movements. The model is then able to output movement coefficients, which can then be used to modify an image file that is representative of the user's body part on which the device is being worn. In this sense, the embodiments can be thought of as performing a modification to a surface reconstruction image, and the embodiments are not performing image-based tracking or strain gauge analysis.

The RF sensors track and monitor conductive material, such as the salt water, blood, muscle groups, etc. in or on the user's body. The RF sensors do not necessarily track the user's skin movement or stretching because skin is not a very conductive material. In this manner, the RF sensors are monitoring conductive material that is included in or on a person's body. The embodiments are able to generate a waveform based on the detected frequencies that are observed by the RF sensors. Stated differently, the RF sensors are designed to oscillate at a particular frequency. As the conductive material inside or on the user's body moves either closer or farther from the RF sensors, the resulting waveform generated by the RF sensors will be modified as discussed above. This change to the waveform can be correlated with the user's movement, thereby enabling the system to determine how the user moved.

Figure 3C:
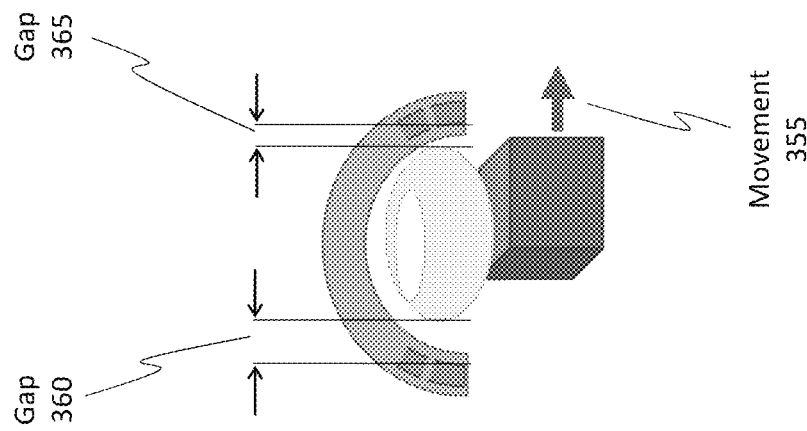
Figure 3C:
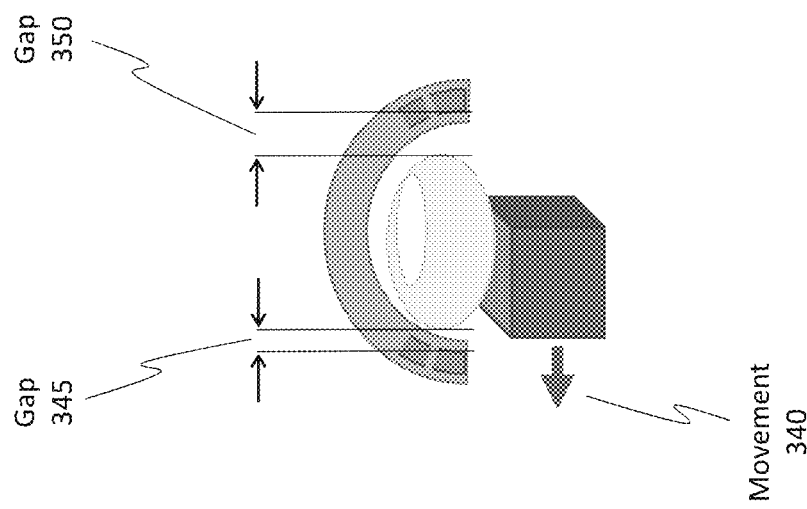

FIG. 3C shows two additional scenarios involving movement of a user's body part. A first movement 340 results in a first set of gaps (e.g., gap 345 and gap 350) between the user's conductive matter and the RF sensors. A second movement 355 results in a second set of gaps (e.g., gap 360 and gap 365) between the user's conductive matter and the RF sensors.

By performing the above operations, the embodiments are able to obtain input from the user with regard to how to control or manipulate holograms displayed by an MR system. In some embodiments, the RF sensors on the device are also able to detect a thumb hovering type of input.

In an example case involving an MR keyboard, the MR system can project a light blue glow over the MR keyboard to show the hovering location of the thumb. At the same time, a rectangular shaped box can be displayed to show the active area of the keyboard with respect to the input device. This enables a faster, more intuitive typing experience in MR as compared to a classic pointer and clicker.

Clippable Units

Figure 4A:
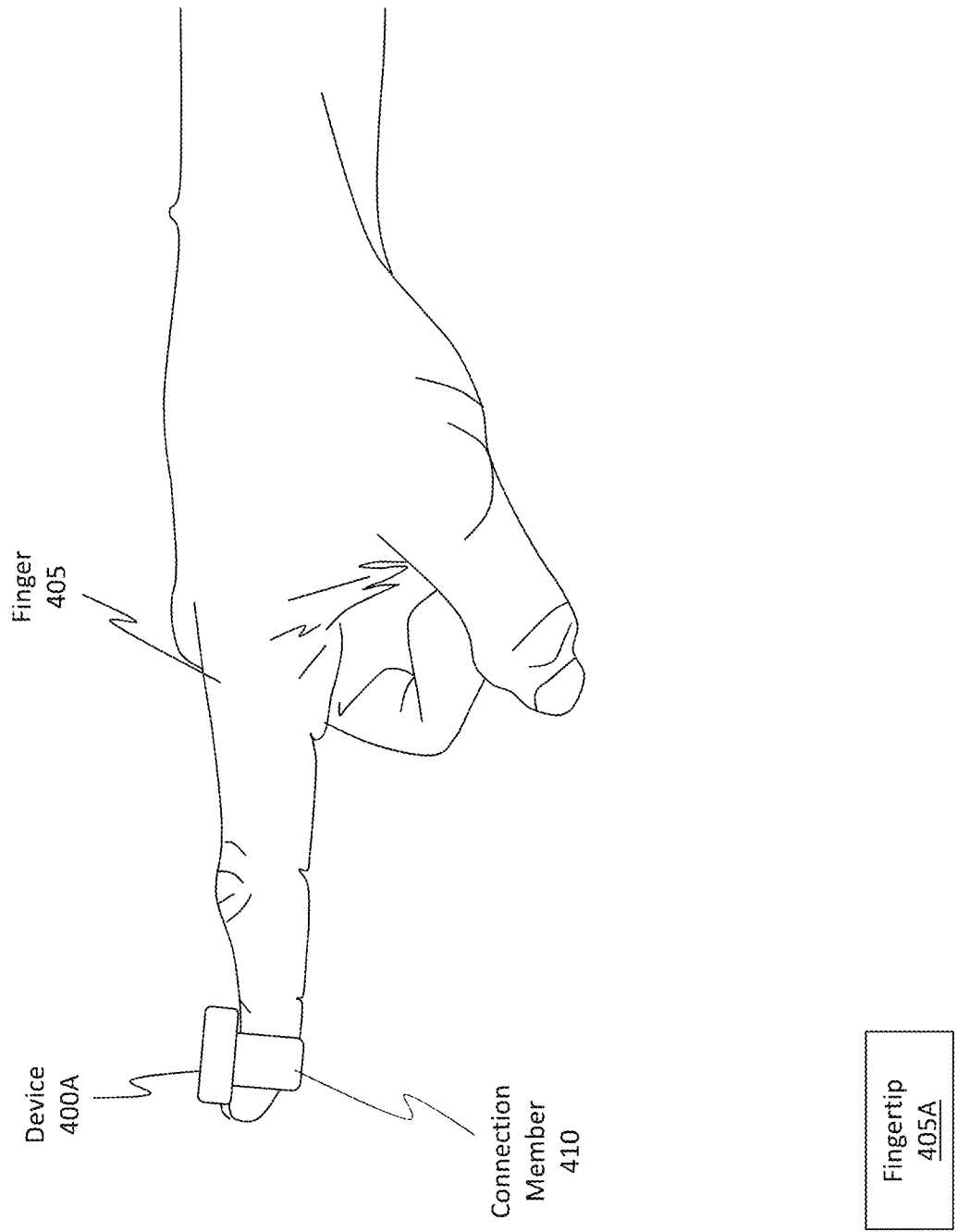
FIGS. 4A, 4B, and 4C illustrate various other features of the wearable device.
Figure 4B:
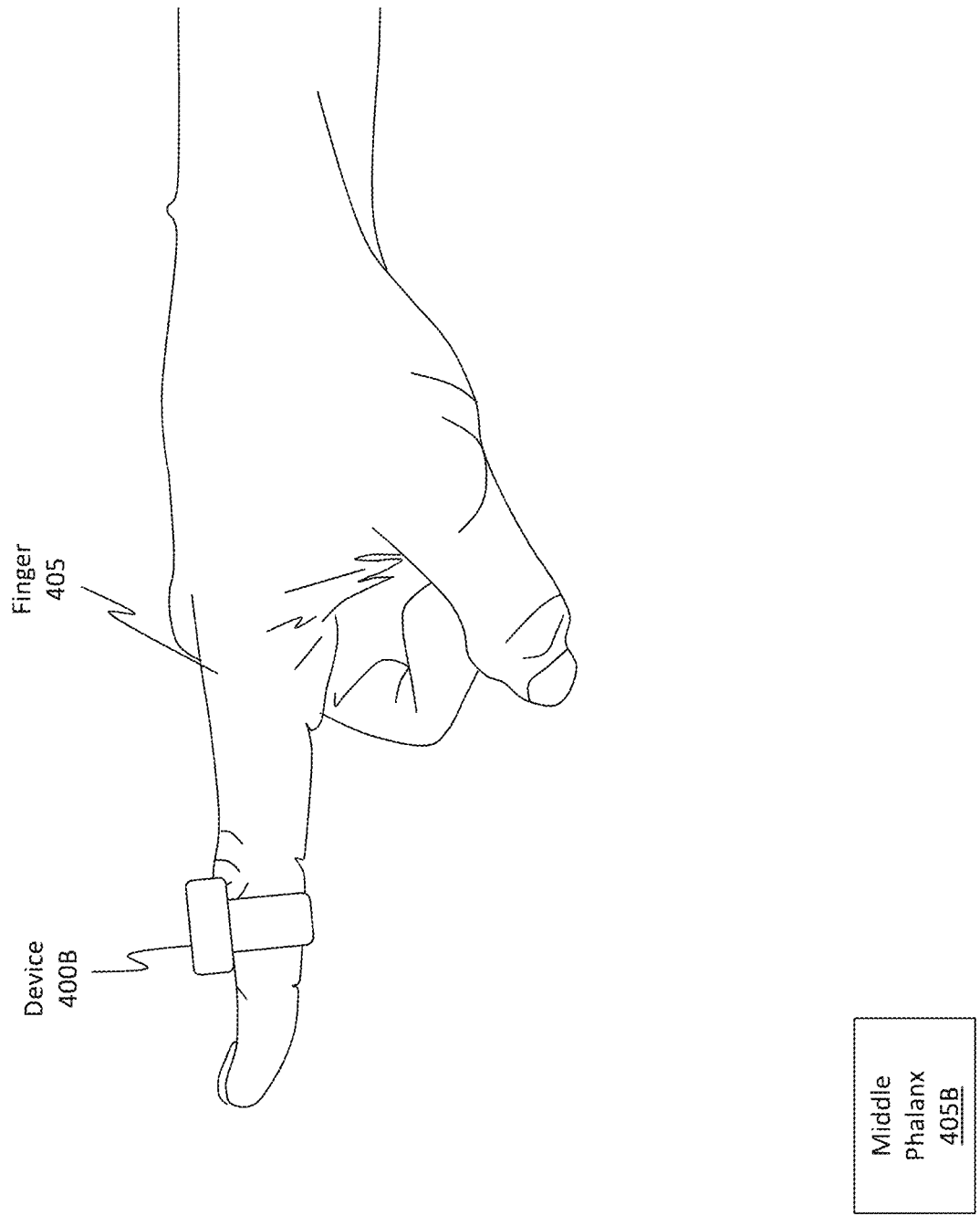
Figure 4C:
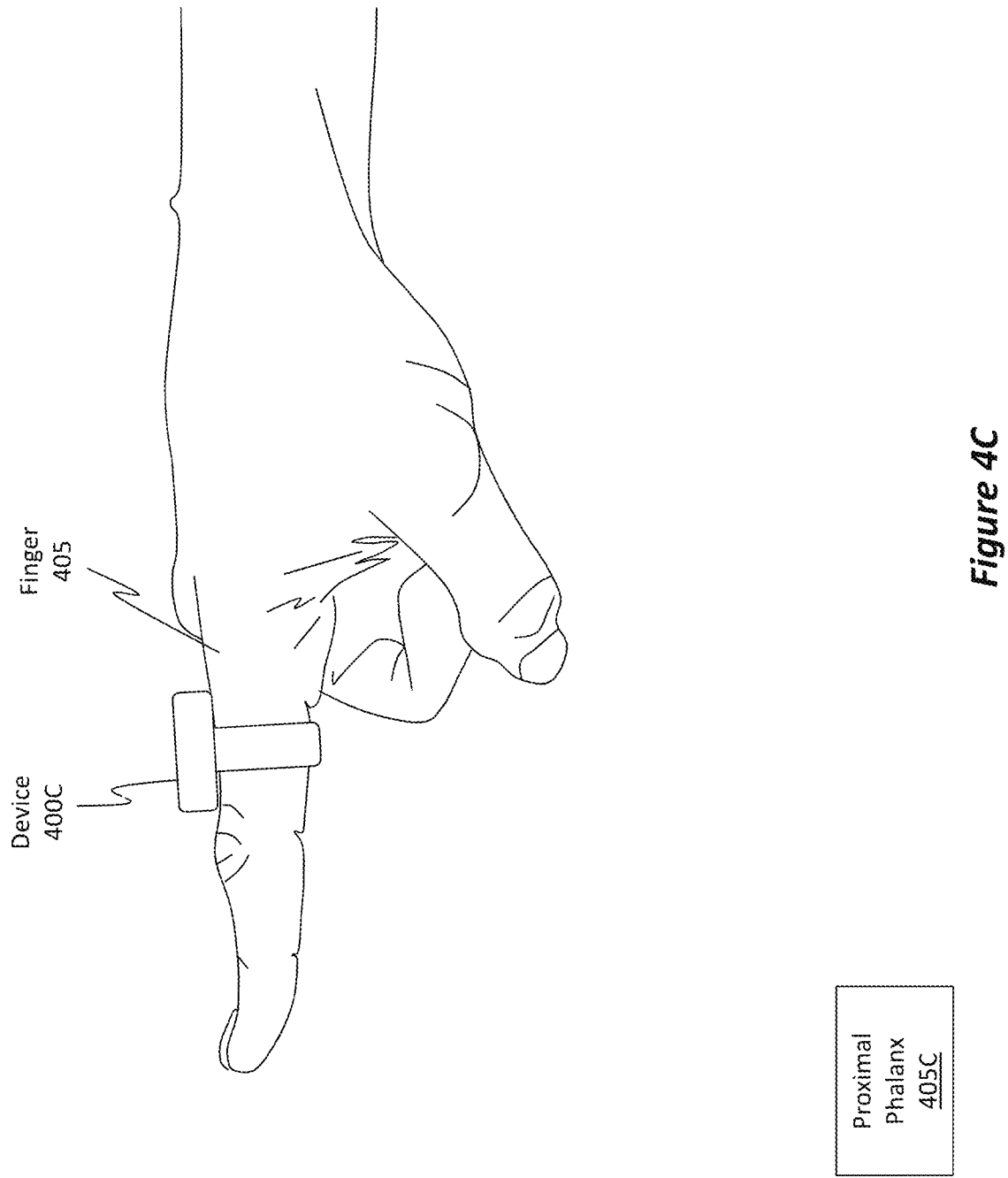

FIGS. 4A, 4B, and 4C show various different example scenarios of how the wearable device can be clipped to the user's body. In these depictions, the wearable device is clipped to the user's finger. One will appreciate, however, how the wearable device can be clipped or otherwise affixed to any part of the user's body, without limit. In some cases, the wearable device can include an elastomeric band that wraps around a portion of the user's body. Thus, instead of a clip mechanism, the wearable device can be worn via an elastic or some other connection member. In some embodiments, the wearable device can be clippable or attached to at least one of: a waist of the user, a wrist of the user, a chest of the user, a neck of the user, an arm of the user, or a leg of the user.

FIG. 4A shows a device 400A, which is representative of the devices mentioned thus far. In this scenario, the device 400A is clipped or otherwise attached to the end of the user's finger 405 (i.e. a fingertip 405A of the user's finger). FIG. 4A shows a connection member 410 that enables the device 400A to be clipped or otherwise attached to the user.

FIG. 4B shows a device 400B. In this scenario, the device 400B is attached or clipped to a middle region of the user's finger 405 (i.e. a middle phalanx 405B of the user's finger).

FIG. 4C shows a device 400C. In this scenario, the device 400C is attached or clipped to a proximal phalanx 405C of the user's finger 405.

Figure 5A:
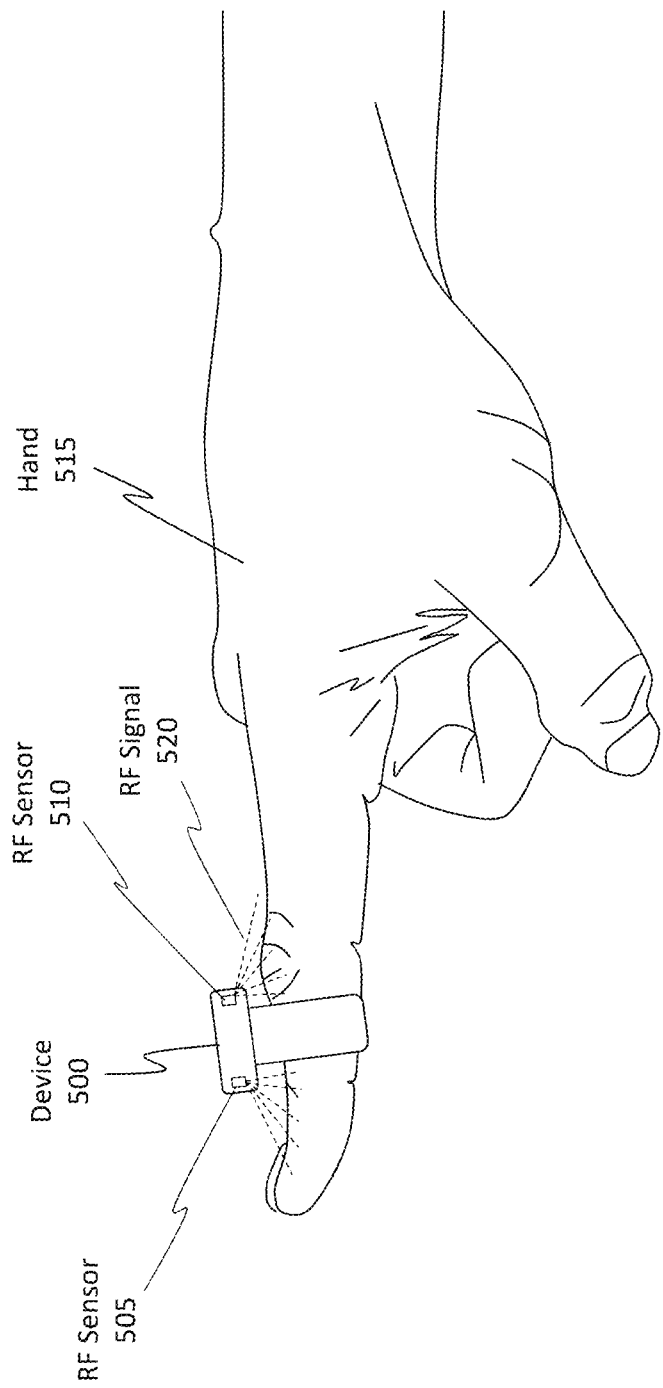
FIGS. 5A and 5B illustrate various operations of the wearable device.

FIG. 5A shows a device 500 comprising a first RF sensor 505 and a second RF sensor 510. It should be noted how any number of RF sensors can be included in the device. For instance, the device can include 1, 2, 3, 4, 5, 6, 7, 8, 9, 10, 20, 30, or more than 30 RF sensors.

The device 500 is shown as being clipped to the user's hand 515, or more particularly to the user's finger. The RF sensor 510 is shown as emitting an RF signal 520. The embodiments are able to track and monitor the peaks and valleys of the resulting waveform that is generated based on the scattering parameters associated with this RF signal 520. It should be noted how the RF sensors do not rely on image data; furthermore, the RF sensors can be structured so as to omit a strain gauge and an image sensor. Thus, the RF sensors rely on the RF signal as opposed to other types of data input. When the user's finger is completely extended, as shown in FIG. 5A, the RF sensor's sensing values may be at its maximum intensity due to the conductive material moving relative to the sensors.

Figure 5B:
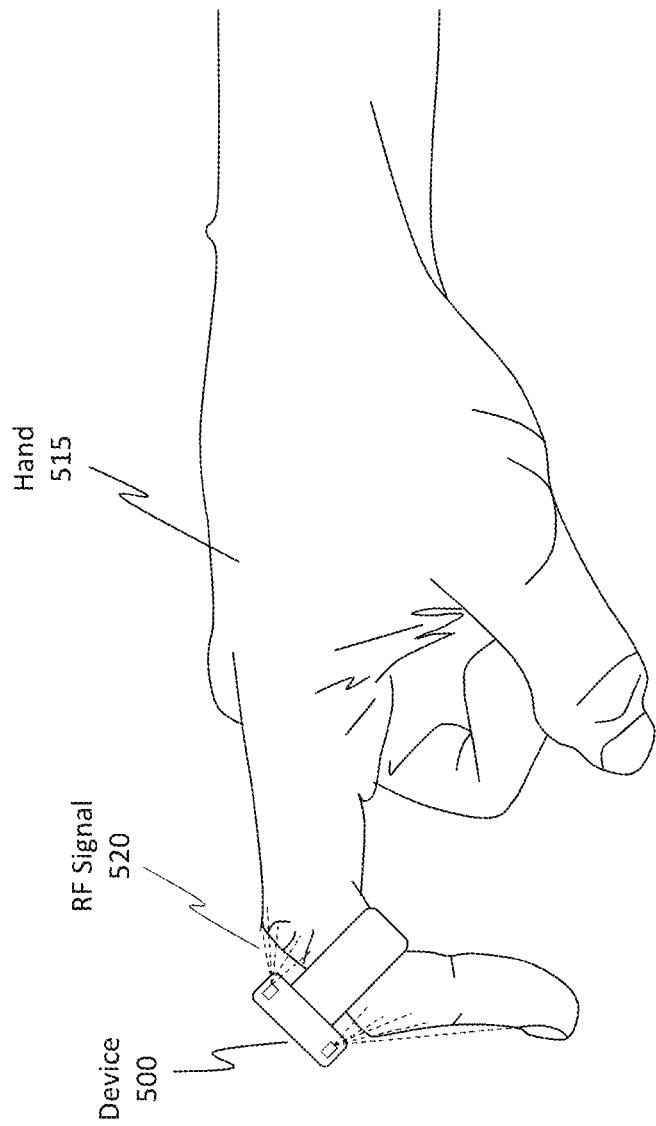

FIG. 5B now shows a scenario where the user's finger is bent. Notice, the RF signal 520 is shown as being different due to the movement of the user's finger. The resulting waveform will similarly change to reflect the distance change between the RF sensor and the conductive matter in the user's finger. When the user's finger curls, as shown in FIG. 5B, the RF sensor's sensing values may decrease in intensity due to the conductive material moving relative to the sensor. This enables the embodiments to detect and predict how much the user's finger is curling.

In some cases, the wearable device can optionally act as a laser point in an MR scene. For instance, the laser pointer may be triggered when the user's finger is fully extended. The laser may be deactivated automatically once the user's finger enters a curled state.

Traditional finger articulation detection is enabled only by the use of cumbersome strain gauge enabled gloves that run along finger. The disclosed embodiments enable a much smaller and easy-to-clean form factor, resulting in significant improvements to tracking technology.

Figure 6:
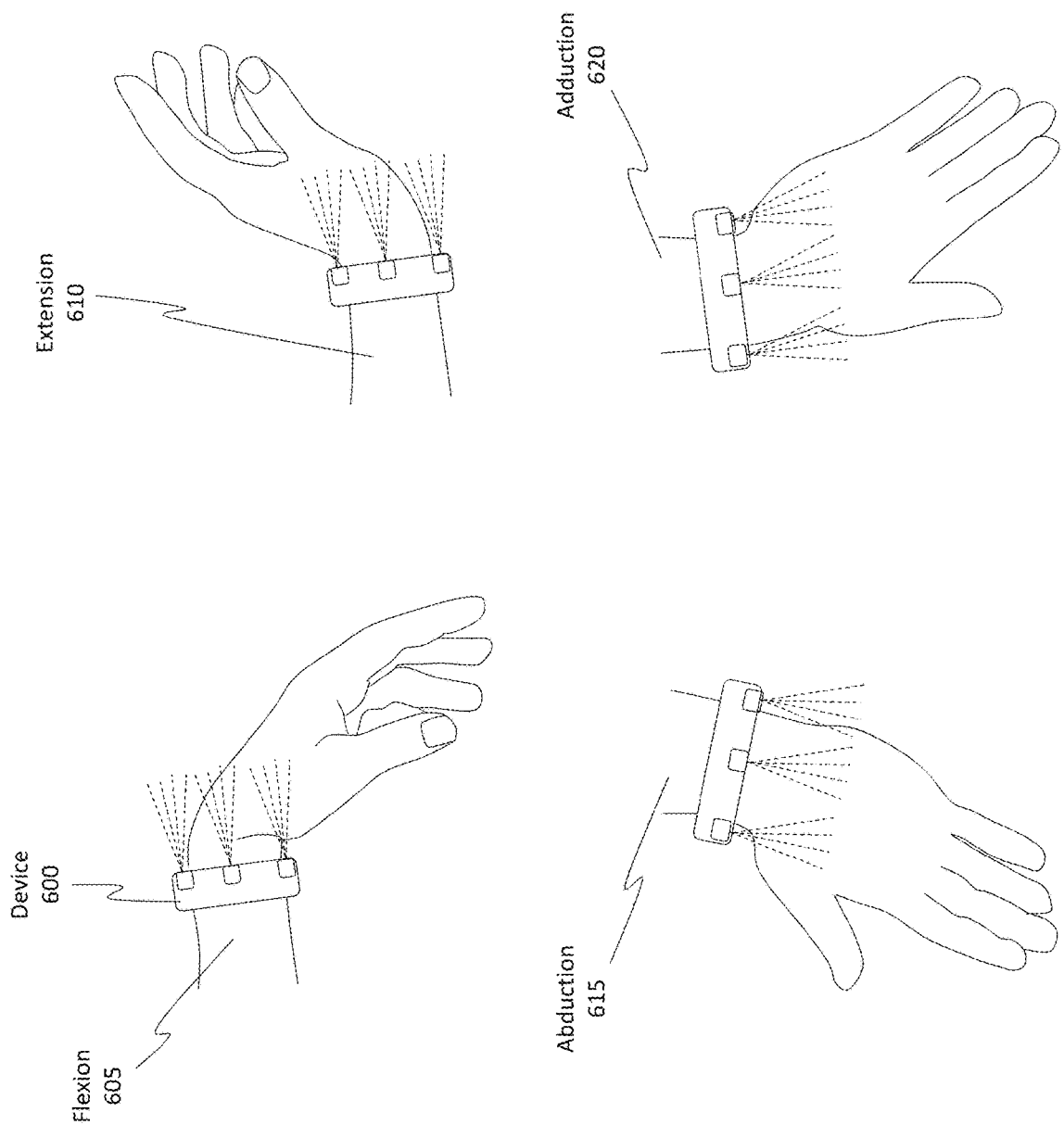
FIG. 6 illustrates a different implementation of the wearable device.
Figure 7B:
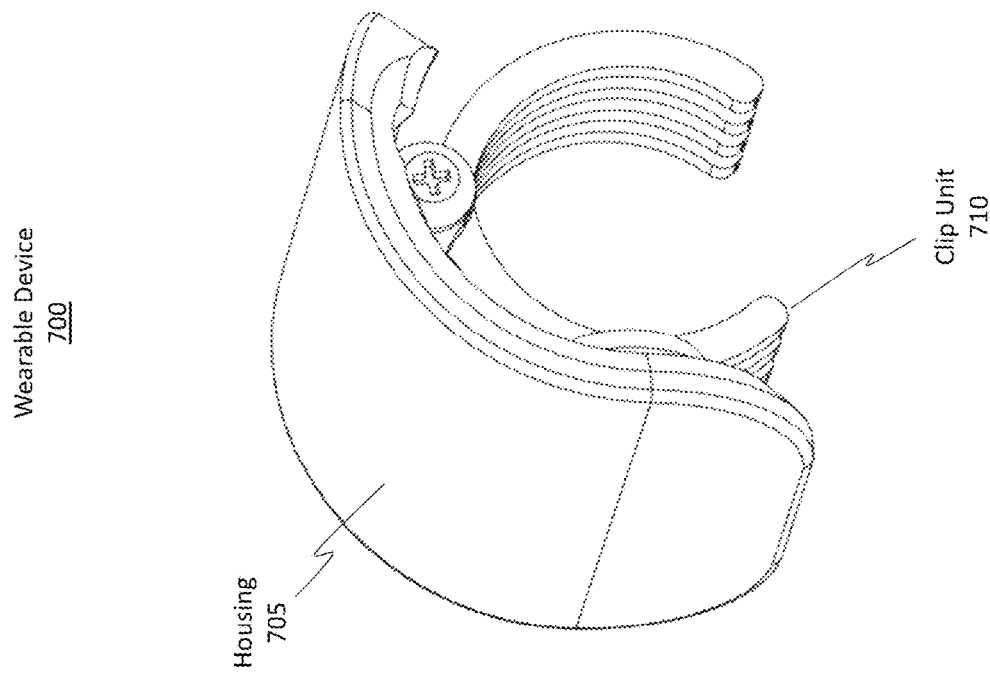
FIGS. 7A, 7B, 7C, 7D, and 7E illustrate various features of the wearable device.
Figure 7A:
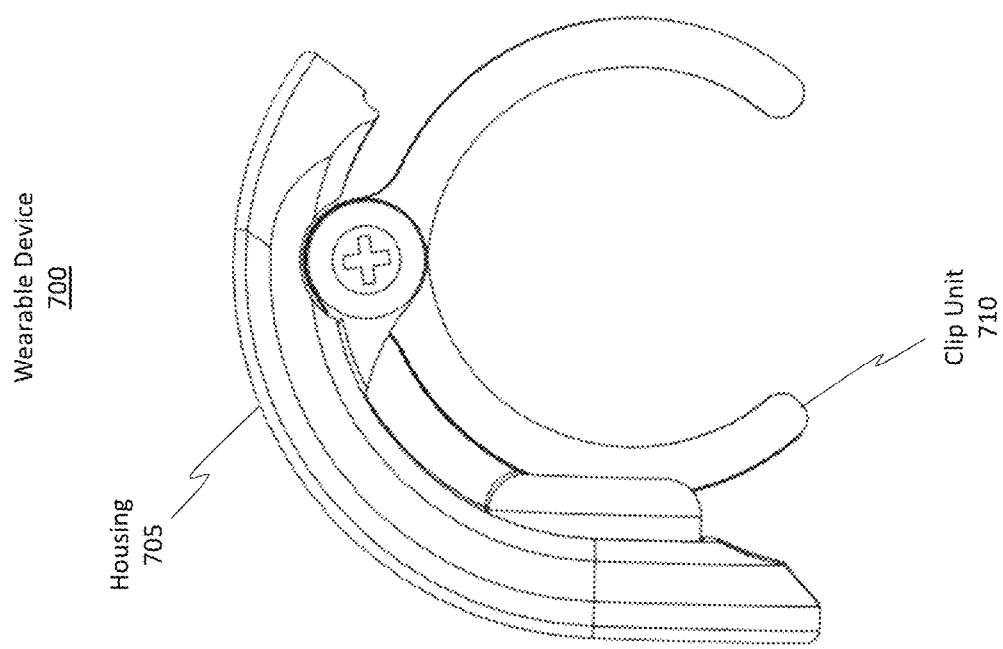
Figure 7D:
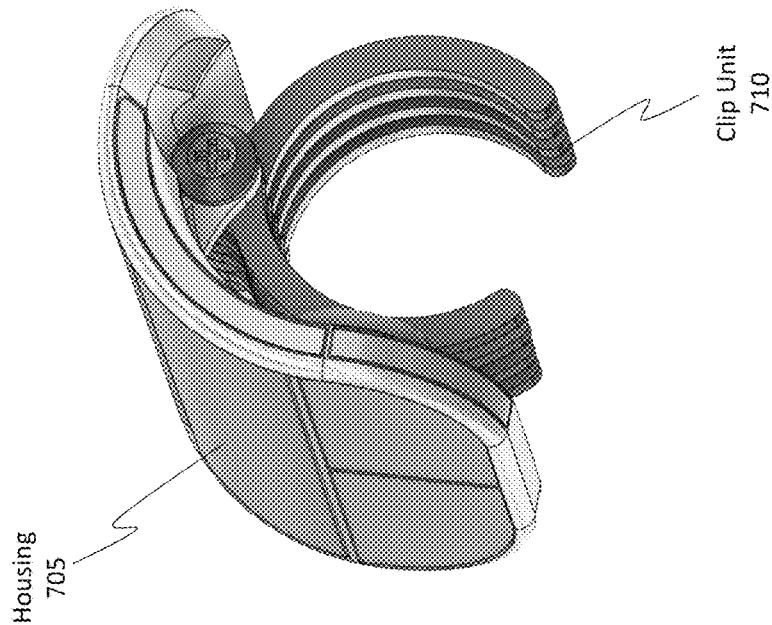
Figure 7C:
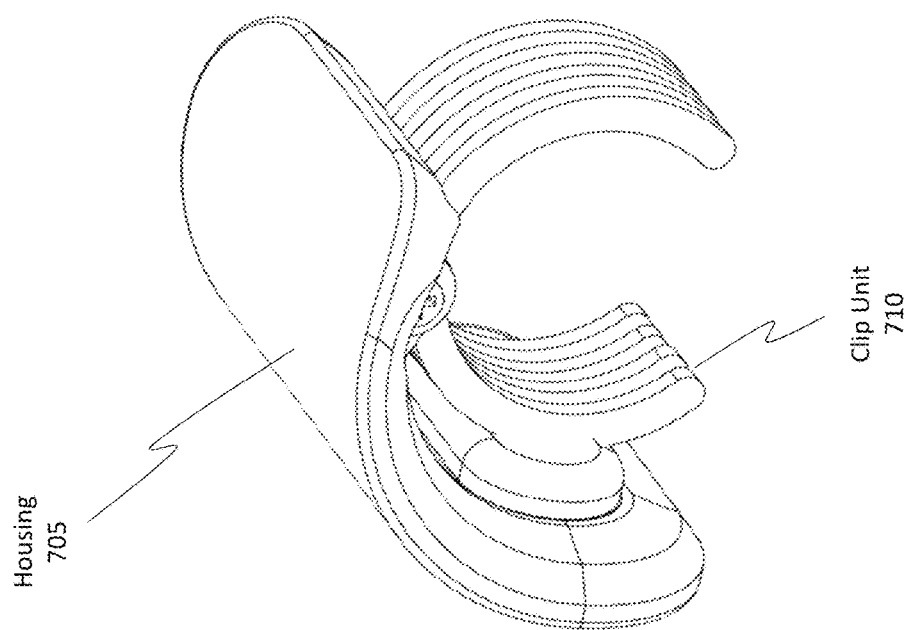
Figure 7E:
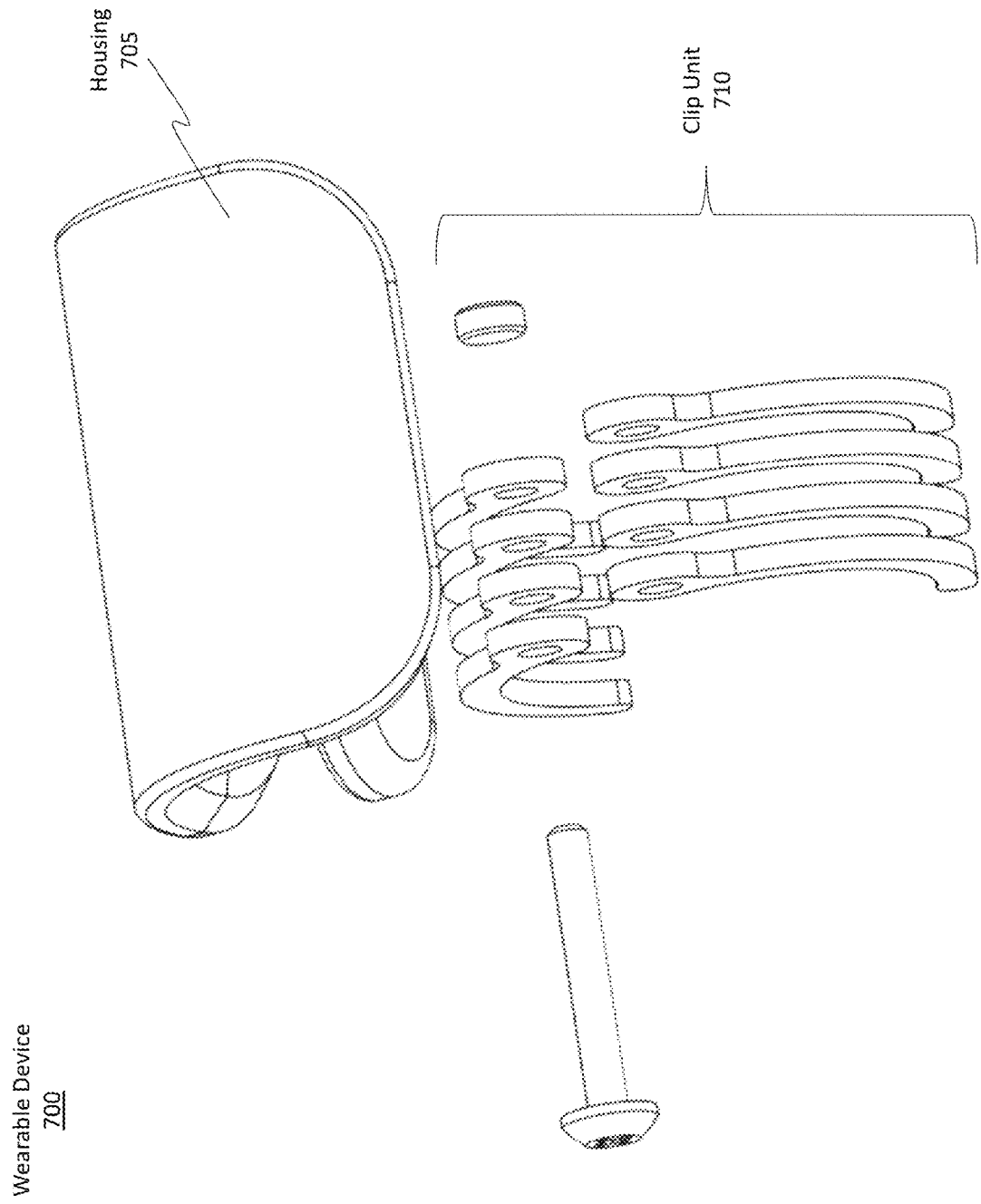

FIG. 6 shows an alternative scenario where a device 600 is clipped or otherwise attached to a user's wrist. The device 600 is shown as emitting various RF signals. Those RF signals change based on the movements of the user's wrist. For instance, the user's wrist can move in different ways, as shown by flexion 605, extension 610, abduction 615, and adduction 620. Accordingly, the wearable device can track one or more of a flexion, an extension, an abduction, or an adduction of the user's muscle group or body part.

Accordingly, in some implementations, the same technological approach can be applied in a wrist-wearable form factor. In some cases, a minimum of 4 sensing electrodes (i.e. RF sensors) are positioned at the top, bottom, and two sides of the device. The near-field sensing capabilities are able to measure the angle at which the wrist is flexing or extending, based on the integration between top and bottom sensor values. The same thing can be done for detecting abduction or adduction.

FIGS. 7A, 7B, 7C, 7D, and 7E illustrate various different perspective views of a wearable device 700 that includes a housing 705 and a clip unit 710, which can also be considered as being a connection member. The RF sensors mentioned previously are disposed inside or on the housing 705. The clip unit 710 includes one or more different clips that are adjustable to accommodate different sized appendages. In this example scenario, the wearable device 700 is a type of device that is worn on a user's finger. The clip unit 710 can expand and contract to accommodate different sizes of fingers. As shown, the clip unit 710 can optionally be made of concentric, half-ring shaped pins, held together via a friction hinge.

Optionally, the embodiments can enable the user to flip the device on the user's body part and/or move the device to a different position on the user's body part, thereby expanding or contracting the rings. Doing so, in some implementations, can automatically turn off the device to save power. That is, the contraction or expansion of the concentric rings can be used to trigger when the device is turned on or off. The device can be reactivated or turned back on by pushing it down to its intended position or by turning it back over.

The wearable device includes a connection member that enables the device to be clipped or otherwise attached to the user's body part. The connection member can include the clip unit mentioned above. In some cases, the connection member can include an elastomeric band or material that wraps around a portion of the user.

The wearable device can be clippable over clothing worn by the user. The wearable device can track the movement of conductive matter (e.g., a muscle group) even when the clothing is disposed between the wearable device and the conductive matter. It should be noted how the wearable device refrains from tracking skin movement of the user; rather, the wearable device tracks the distance or gap that exists between the device's RF sensors and conductive matter that is included as a part of or on top of the user's body. Generally, skin is not very conductive. The conductive matter can be one or more of: a muscle group of the user, blood of the user, salt water of the user, or any other conductive matter in or on the user's body. In some cases, as mentioned, a paste or lotion that is conductive can be applied to the user's skin, and the RF sensors can track the movement of that lotion.

Example Architecture

Figure 8:
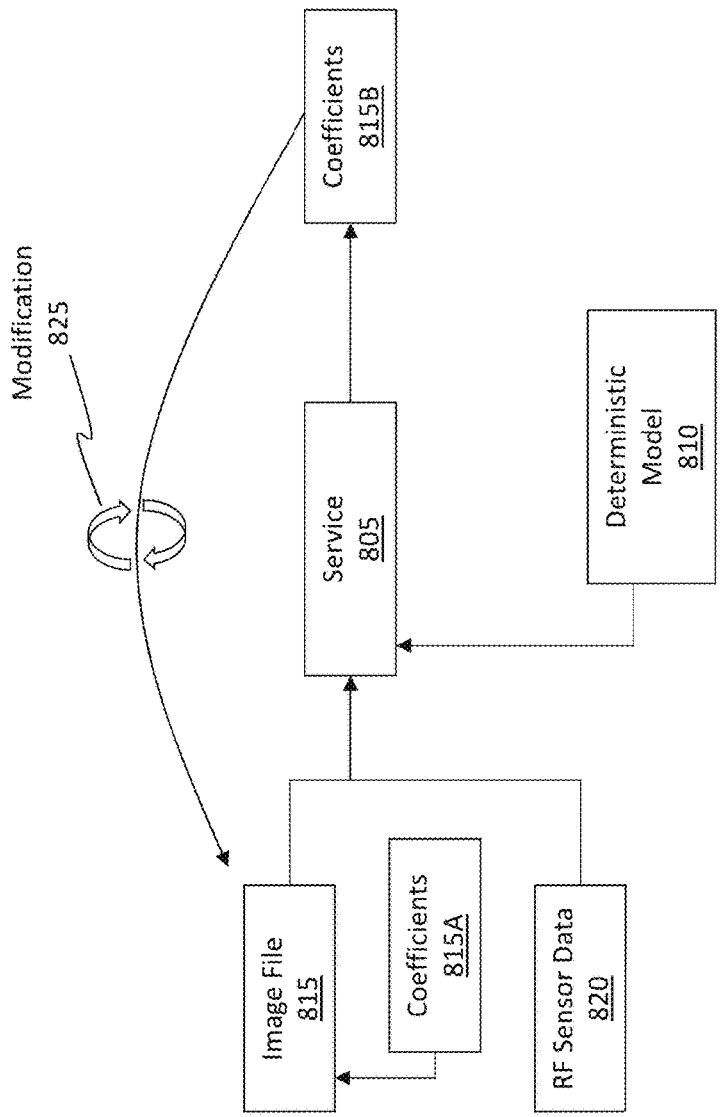
FIG. 8 illustrates an example architecture that is able to use data obtained from the wearable device to perform various actions.

Attention will now be directed to FIG. 8, which illustrates an example architecture 800 that can be used to interpret how conductive matter in or on a person's body moves. Such interpretation can beneficially be used to improve how a user interacts with holograms displayed by an MR system, as was shown in FIG. 2.

Architecture 800 can optionally be implemented on the MR devices mentioned earlier. Architecture 800 includes a service 805. As used herein, the term service refers to a programming construct that is designed to perform specific, automated tasks. In some cases, service 805 can be implemented in a cloud environment such that service 805 is a cloud-based service. In some cases, service 805 can be implemented locally on a device, such as the HMD. In some cases, service 805 can be a hybrid service that includes a cloud-based component and a local component.

Service 805 can include a deterministic model 810. The deterministic model 810 should be viewed as being distinct relative to a machine learning (ML) engine or any form of artificial intelligence engine. In some cases, however, the service 805 can optionally include an ML engine.

As used herein, the deterministic model 810 is a type of model that enables the service 805 to calculate or determine a future event exactly, without a random factor being included in the calculation. To be "deterministic," then, the model has all of the data that is needed to fully complete the calculation.

The service 805 is generally tasked with determining how a body part of a user is moving. More specifically, the service 805 can be tasked with monitoring the movement of conductive matter associated with the user's body and then providing an interpretation regarding that movement so that a subsequent action can be performed. The term "associated" should be interpreted broadly as being one thing being linked, connected, or otherwise related to another thing. For instance, the muscles and tendons of a user's finger are "associated" with that user's finger because a relationship exists between that particular body part of the user and the underlying musculoskeletal features. As an example, the service 805 can monitor a pinching movement of a user's finger by monitoring the expansion and contraction of the user's muscle groups in the user's finger. This pinching movement can then be correlated with a hologram displayed by an MR system. The hologram can then be manipulated based on the pinching movement.

To facilitate such operations, service 805 generates or accesses an image file 915 corresponding to the body part on which the wearable device mentioned earlier is clipped or otherwise attached to. An example of the image file 815 can optionally be a computer-aided design (CAD) file. The image file 815 includes any number of coefficients 815A. Modification of these coefficients 815A results in a modification to the visualization of the image file 815. As an example, the image file 915 may include a detailed representation of a finger. The coefficients 815A reflect various properties and characteristics with regard to how the finger is portrayed or rendered in the image file 815. In one scenario, a set of coefficients may correspond to the various finger joints. Modification of the coefficients can result in the finger being displayed in an extended state or a curled stated.

It should be noted that the image file 815 can be a template image and need not be one that is specifically customized to reflect actual features of the user's body part. In this regard, the same image can be used for multiple different users.

In some cases, however, the image file 815 may accurately depict a specific user's body part. For instance, a rendering of the user's actual body part can be obtained and used as the image 815. Typically, however, the image file 815 is a type of template image that can be used regardless of what user is using the MR system and the wearable device.

Initially, the image file 815 may correspond to a resting pose of the user's body part, where (as mentioned previously) a "resting pose" is a pose that can be thought of as a default pose or an initial baseline pose of the user's body part. Modifying the coefficients can result in the image file 815 being modified to reflect a version of the user's body part based on a detected movement of the user's body part. Thus, modifying a select set of the coefficients 815A can result in changes to how the user's body part is visualized in the image file 815.

FIG. 8 shows how the service 805 is able to obtain or access RF sensor data 820 obtained from the RF sensors included in the wearable device. In scenarios where the service 805 is implemented in an MR system, the MR system can communicate with the wearable device via any communication technique, such as Bluetooth, near field communication, and so on.

The RF sensor data 820 includes a set of scattering parameter data. The service 805 uses the RF sensor data 820 to generate a modified version of the image file's coefficients, as shown by coefficients 815B. These coefficients 815B are then used to modify the image file 815, as shown by modification 825. Optionally, all or a portion of the modified image file can then be displayed on the MR system, such as in the form of a hologram. Regardless of how the display occurs, the movements that are tracked using the wearable device can be used to enable the user to interact with other holograms that are displayed by the MR system.

The embodiments are able to change the image file element by element and vertex by vertex, resulting in an image that is fully customized to the movements of the user. If a wearable device is clipped to a person's finger, the embodiments are able to display how the person's finger moves in the MR system's display.

The granularity by which the image file can be modified can be dependent on the number of RF sensors that are available in the wearable device. A larger number of RF sensors allows for more information to be collected, thereby resulting in a more specific tailoring or modification of the image file's coefficients. As a result, a more customizable image can be generated and optionally displayed.

Example Methods

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

Figure 9:
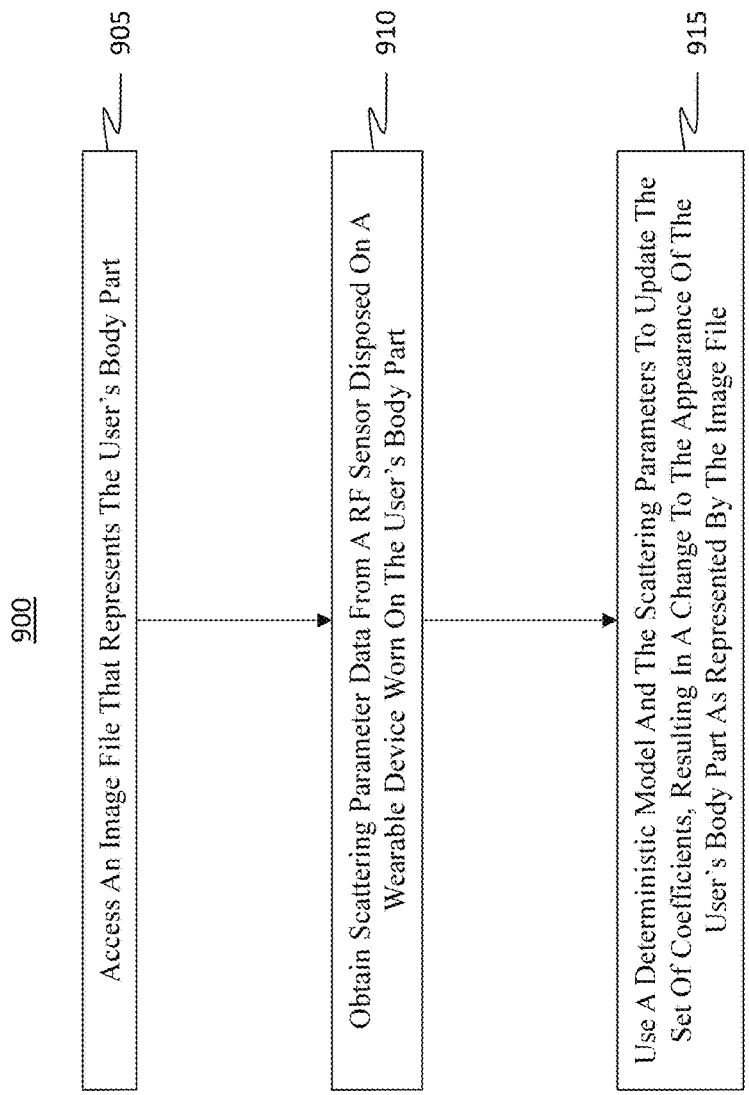
FIG. 9 illustrates a flowchart of an example method for tracking a movement of a user's body part using a wearable device.

Attention will now be directed to FIG. 9, which illustrates a flowchart of an example method 900 for modifying an image file of a body part of a user to reflect a movement of the user's body part. Method 900 can be implemented in the architecture 800 of FIG. 8. Furthermore, method 900 can be performed by the service 805. Even further, method 900 can be facilitated via use of the disclosed wearable devices.

The disclosed wearable devices are structured or configured to monitor movement of conductive matter (e.g., perhaps a muscle group, blood, salt water, etc.) of a user who is wearing the device. The device can include a housing and a clip. The clip is attached to the housing, and the clip enables the wearable device to be coupled to a body part of the user. This body part is associated with the conductive matter.

The device further includes a radio frequency (RF) sensor that is disposed in the housing. The RF sensor is caused to oscillate at one of a plurality of available preselected frequencies. The RF sensor is tuned to resonate when the RF sensor is located a preselected distance from the user's conductive matter while the wearable device is clipped to the user's body part. As the user's conductive matter moves closer or farther from the RF sensor based on the movement of the user's conductive matter, a resulting waveform generated based on data from the RF sensor is modified, and the resulting waveform is usable to determine how the user's conductive matter moved.

As indicated above, method 900 can use the sensor data generated by the wearable device. Method 900 includes an act (act 905) of accessing an image file that represents the user's body part. This image can be a general template image, or it can be one customized to this specific user. The image file includes a set of coefficients that, if modified, changes an appearance of the body part as it is represented by the image file.

Act 910 includes obtaining scattering parameter data from a radio frequency (RF) sensor disposed on a wearable device worn on the user's body part. The RF sensor generates a set of scattering parameters that reflect a movement of conductive matter associated with the user's body part. The conductive matter can be located underneath the user's skin; it can also optionally be located on the user's skin in the form of a cream or lotion or other on-skin material.

Act 915 includes using a model (e.g., a deterministic model, though an AI model can also optionally be used) and the scattering parameters to update the set of coefficients. Such an action results in a change to the appearance of the body part as it is represented by the image file.

In some cases, the movement of the conductive matter is performed outside of a field of view (FOV) of a camera of a mixed-reality (MR) system that is communicating with the wearable device. Despite not being in the camera's FOV, the embodiments are still able to track the movement because the tracking operations are not dependent on image data. Also, in some implementations, the set of scattering parameters are used to generate a waveform that tracks peaks and valleys of a frequency change detected by the RF sensor.

Accordingly, hand and body part tracking has seen significant progress in the last few years. However, traditional tracking techniques often fail to operate or detect actions performed outside of the MR system's cameras' fields of view. This means that for body part tracking to work well (according to traditional techniques), the user's hands need to be in the view of the camera. Even with wider fields of view promised by new hardware, there is no escape from the tiresome act of having the user hold his/her hands up for long periods of time (aka Gorilla Arm Syndrome). One alternative option is to use a 6 degree of freedom (DOF) tracking controller. Yet, the biggest problem with the current controllers is that they undermine the core experience of AR in that they stop the user from interacting directly with the real world. Traditional techniques that rely solely on hand tracking also resulted in only auditory feedback being provided to the user. This greatly limits the feeling of immersion that augmented and virtual reality systems aims for.

Most interactions performed through hand tracking involve interactions between the user's index and thumb. The disclosed solutions present a compact device that can sit on the dorsal middle phalanx of a user's index finger. In some embodiments, the disclosed device includes 9 electrodes (or "antennas" or "RF sensors") connected to a small board that produces 9 float values (i.e. RF signals). The change in RF signals relates to the physical relationship between the index finger and thumb. This makes it significantly easier to detect pinches, scrolls, and swipes, even when the hand is outside of the tracking camera's field of view.

The device can also deliver localized haptic feedback for a more immersive experience. The device can also detect palmar touches, turning the index palmar phalanxes into input buttons. These could be used for quick key buttons such as "home" or "go back" command.

Traditional AR/VR input devices on the market can be divided between bulkier gaming-focused controllers and smaller finger-worn devices. Finger-worn devices have struggled to provide enough value from a tracking perspective, having focused mainly on capacitive touch surface for "scrolling" interactions. VR controllers have a much larger form factor and therefore can provide accurate input tracking and input button functionalities. However, they have mainly been focused on gaming applications, as having to carry around two controllers is not ideal for subtle, everyday AR interactions.

The disclosed solutions deliver accurate tracking of the user's body, including the user's index finger, middle finger, thumb, or any other body part while also accurately detecting different movements (e.g., pinches, surface taps, etc.). This is all delivered by the disclosed RF sensing technology while also reducing device power consumption.

Example Computer/Computer Systems

Figure 10:
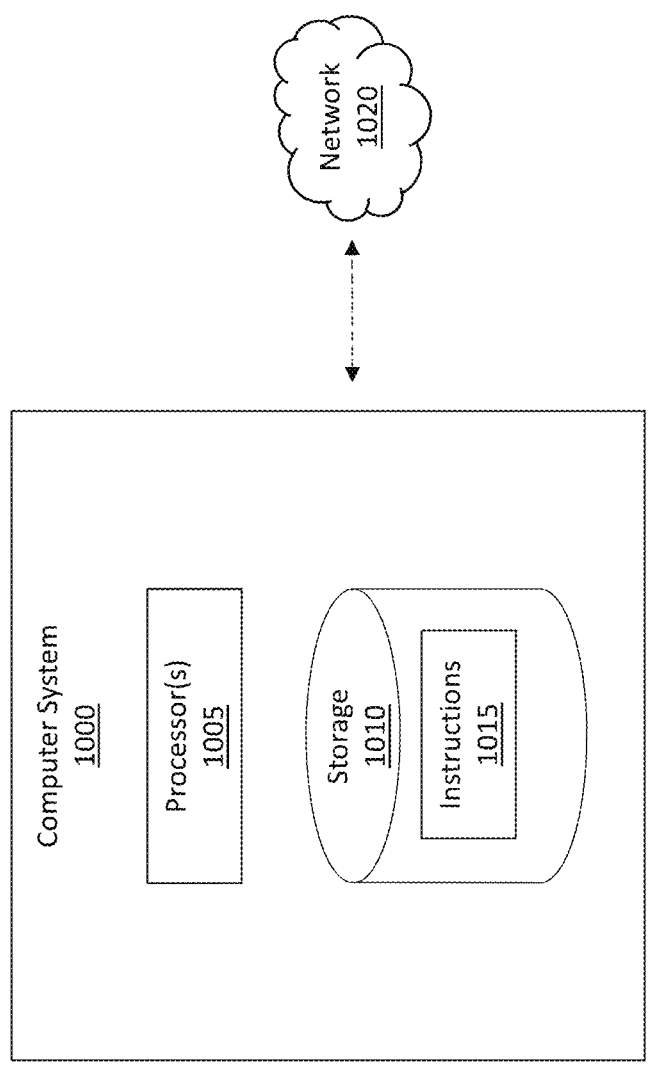
FIG. 10 illustrates an example computer system capable of performing any of the disclosed operations.

Attention will now be directed to FIG. 10 which illustrates an example computer system 1000 that may include and/or be used to perform any of the operations described herein. For instance, computer system 1000 can implement the service 805 of FIG. 8. Furthermore, the disclosed HMDs can be implemented in the form of computer system 1000.

Computer system 1000 may take various different forms. For example, computer system 1000 may be embodied as an HMD, a tablet, a desktop, a laptop, a mobile device, or a standalone device, such as those described throughout this disclosure. Computer system 1000 may also be a distributed system that includes one or more connected computing components/devices that are in communication with computer system 1000.

In its most basic configuration, computer system 1000 includes various different components. FIG. 10 shows that computer system 1000 includes one or more processor(s) 1005 (aka a "hardware processing unit") and storage 1010.

Regarding the processor(s) 1005, it will be appreciated that the functionality described herein can be performed, at least in part, by one or more hardware logic components (e.g., the processor(s) 1005). For example, and without limitation, illustrative types of hardware logic components/processors that can be used include Field-Programmable Gate Arrays ("FPGA"), Program-Specific or Application-Specific Integrated Circuits ("ASIC"), Program-Specific Standard Products ("ASSP"), System-On-A-Chip Systems ("SOC"), Complex Programmable Logic Devices ("CPLD"), Central Processing Units ("CPU"), Graphical Processing Units ("GPU"), or any other type of programmable hardware.

As used herein, the terms "executable module," "executable component," "component," "module," or "engine" can refer to hardware processing units or to software objects, routines, or methods that may be executed on computer system 1000. The different components, modules, engines, and services described herein may be implemented as objects or processors that execute on computer system 1000 (e.g. as separate threads).

Storage 1010 may be physical system memory, which may be volatile, non-volatile, or some combination of the two. The term "memory" may also be used herein to refer to non-volatile mass storage such as physical storage media. If computer system 1000 is distributed, the processing, memory, and/or storage capability may be distributed as well.

Storage 1010 is shown as including executable instructions 1015. The executable instructions 1015 represent instructions that are executable by the processor(s) 1005 of computer system 1000 to perform the disclosed operations, such as those described in the various methods.

The disclosed embodiments may comprise or utilize a special-purpose or general-purpose computer including computer hardware, such as, for example, one or more processors (such as processor(s) 1005) and system memory (such as storage 1010), as discussed in greater detail below. Embodiments also include physical and other computer-readable media for carrying or storing computer-executable instructions and/or data structures. Such computer-readable media can be any available media that can be accessed by a general-purpose or special-purpose computer system. Computer-readable media that store computer-executable instructions in the form of data are "physical computer storage media" or a "hardware storage device." Furthermore, computer-readable storage media, which includes physical computer storage media and hardware storage devices, exclude signals, carrier waves, and propagating signals. On the other hand, computer-readable media that carry computer-executable instructions are "transmission media" and include signals, carrier waves, and propagating signals. Thus, by way of example and not limitation, the current embodiments can comprise at least two distinctly different kinds of computer-readable media: computer storage media and transmission media.

Computer storage media (aka "hardware storage device") are computer-readable hardware storage devices, such as RAM, ROM, EEPROM, CD-ROM, solid state drives ("SSD") that are based on RAM, Flash memory, phase-change memory ("PCM"), or other types of memory, or other optical disk storage, magnetic disk storage or other magnetic storage devices, or any other medium that can be used to store desired program code means in the form of computer-executable instructions, data, or data structures and that can be accessed by a general-purpose or special-purpose computer.

Computer system 1000 may also be connected (via a wired or wireless connection) to external sensors (e.g., one or more remote cameras) or devices via a network 1020. For example, computer system 1000 can communicate with any number devices or cloud services to obtain or process data. In some cases, network 1020 may itself be a cloud network. Furthermore, computer system 1000 may also be connected through one or more wired or wireless networks to remote/separate computer systems(s) that are configured to perform any of the processing described with regard to computer system 1000.

A "network," like network 1020, is defined as one or more data links and/or data switches that enable the transport of electronic data between computer systems, modules, and/or other electronic devices. When information is transferred, or provided, over a network (either hardwired, wireless, or a combination of hardwired and wireless) to a computer, the computer properly views the connection as a transmission medium. Computer system 1000 will include one or more communication channels that are used to communicate with the network 1020. Transmissions media include a network that can be used to carry data or desired program code means in the form of computer-executable instructions or in the form of data structures. Further, these computer-executable instructions can be accessed by a general-purpose or special-purpose computer. Combinations of the above should also be included within the scope of computer-readable media.

Upon reaching various computer system components, program code means in the form of computer-executable instructions or data structures can be transferred automatically from transmission media to computer storage media (or vice versa). For example, computer-executable instructions or data structures received over a network or data link can be buffered in RAM within a network interface module (e.g., a network interface card or "NIC") and then eventually transferred to computer system RAM and/or to less volatile computer storage media at a computer system. Thus, it should be understood that computer storage media can be included in computer system components that also (or even primarily) utilize transmission media.

Computer-executable (or computer-interpretable) instructions comprise, for example, instructions that cause a general-purpose computer, special-purpose computer, or special-purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the embodiments may be practiced in network computing environments with many types of computer system configurations, including personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The embodiments may also be practiced in distributed system environments where local and remote computer systems that are linked (either by hardwired data links, wireless data links, or by a combination of hardwired and wireless data links) through a network each perform tasks (e.g. cloud computing, cloud services and the like). In a distributed system environment, program modules may be located in both local and remote memory storage devices.

The present invention may be embodied in other specific forms without departing from its characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A wearable device that monitors movement of a muscle group of a user who is wearing the device, said device comprising:
 a housing;
 a clip, wherein:
  the clip is attached to the housing, and
  the clip enables the wearable device to be coupled to a body part of the user, said body part being associated with the muscle group; and
 a radio frequency (RF) sensor that is disposed in the housing, wherein:

the RF sensor is caused to oscillate at one of a plurality of available preselected frequencies, the RF sensor is tuned to resonate when the RF sensor is located a preselected distance from the user's muscle group while the wearable device is clipped to the user's body part, and as the user's muscle group moves closer or farther from the RF sensor based on the movement of the user's muscle group, a resulting waveform generated based on data from the RF sensor is modified, and the resulting waveform is usable to determine how the user's muscle group moved.

2. The wearable device of claim 1, wherein the plurality of available preselected frequencies are selected from a range of frequencies spanning between about 100 KHz to about 2 GHz.

3. The wearable device of claim 2, wherein the one frequency at which the RF sensor oscillates is one of 200 KHz, 500 KHz, or 1 GHz.

4. The wearable device of claim 1, wherein the RF sensor is caused to perform frequency hopping.

5. The wearable device of claim 1, wherein the wearable device is clippable on a proximal phalanx of the user.

6. The wearable device of claim 1, wherein the wearable device is clippable on a middle phalanx of the user.

7. The wearable device of claim 1, wherein the wearable device is clippable to a fingertip of the user.

8. The wearable device of claim 1, wherein the wearable device is clippable to at least one of: a waist of the user, a wrist of the user, a chest of the user, a neck of the user, an arm of the user, or a leg of the user.

9. The wearable device of claim 1, wherein the wearable device tracks one or more of a flexion, an extension, an abduction, or an adduction of the user's muscle group.

10. The wearable device of claim 1, wherein the wearable device is clippable over clothing worn by the user, and wherein the wearable device tracks the movement of the user's muscle group even when the clothing is disposed between the wearable device and the user's muscle group.

11. The wearable device of claim 1, wherein the wearable device refrains from tracking skin movement of the user.

12. A wearable device that monitors movement of conductive matter of a user who is wearing the device, said device comprising:
   a housing;
   a connection member, wherein:
      the connection member is coupled to the housing, and
      the connection member enables the wearable device to be coupled to a body part of the user, said body part being associated with the conductive matter; and
   a radio frequency (RF) sensor that is disposed in the housing, wherein:
      the RF sensor is caused to oscillate at one of a plurality of available preselected frequencies,
      the RF sensor is tuned to resonate when the RF sensor is located a preselected distance from the user's conductive matter while the wearable device is clipped to the user's body part, and
      as the user's conductive matter moves closer or farther from the RF sensor based on the movement of the user's conductive matter, a resulting waveform generated based on data from the RF sensor is modified, and the resulting waveform is usable to determine how the user's conductive matter moved.

13. The wearable device of claim 12, wherein the conductive matter is one or more of: a muscle group of the user, blood of the user, salt water of the user, or a conductive material disposed on top of skin of the user.

14. The wearable device of claim 12, wherein the wearable device is grounded to the user.

15. The wearable device of claim 12, wherein the wearable device tracks health metrics of the user.

16. The wearable device of claim 15, wherein the health metrics include one or more of: blood pressure of the user, heart rate of the user, respiration rate of the user, glucose level of the user, or a hydration level of the user.

17. The wearable device of claim 12, wherein the wearable device omits a strain gauge and an image sensor.

18. A method for modifying an image file that is representative of a body part of a user to reflect a movement of the user's body part, said method comprising:
   accessing an image file that represents the body part of the user, wherein the image file includes a set of coefficients that, if modified, changes an appearance of the body part as represented by the image file;
   obtaining scattering parameter data from a radio frequency (RF) sensor disposed on a wearable device worn on the body part, wherein the RF sensor generates a set of scattering parameters that reflect a movement of conductive matter associated with the body part; and
   using a model and the scattering parameters to update the set of coefficients, resulting in a change to the appearance of the body part as represented by the image file.

19. The method of claim 18, wherein the movement of the conductive matter is performed outside of a field of view of a camera of a mixed-reality (MR) system that is communicating with the wearable device.

20. The method of claim 18, wherein the set of scattering parameters are used to generate a waveform that tracks peaks and valleys of a frequency change detected by the RF sensor.

* * * * *